US006867212B2

(12) United States Patent
Fujii et al.

(10) Patent No.: US 6,867,212 B2
(45) Date of Patent: Mar. 15, 2005

(54) 6-(1-FLUOROETHYL)-5-IODO-4-AMINOPYRIMIDINE COMPOUNDS PROCESS FOR PREPARATION OF THE SAME AND PEST CONTROLLERS FOR AGRICULTURAL AND HORTICULTURAL USE

(75) Inventors: Katsutoshi Fujii, Ube (JP); Shoji Shikita, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 10/250,971

(22) PCT Filed: Jan. 10, 2002

(86) PCT No.: PCT/JP02/00064

§ 371 (c)(1), (2), (4) Date: Jul. 10, 2003

(87) PCT Pub. No.: WO02/066444

PCT Pub. Date: Aug. 29, 2002

(65) Prior Publication Data

US 2004/0063945 A1 Apr. 1, 2004

(30) Foreign Application Priority Data

Jan. 11, 2001 (JP) ....................................... 2001-003825

(51) Int. Cl.$^7$ .................... C07D 239/42; C07D 405/12; A01N 43/54

(52) U.S. Cl. ........................ 514/256; 544/326; 544/328

(58) Field of Search ................................ 544/326, 328; 514/256

(56) References Cited

FOREIGN PATENT DOCUMENTS

| | | | |
|---|---|---|---|
| JP | 07-101939 | * | 4/1995 |
| JP | 64-68362 A | | 3/1989 |
| JP | 07-101939 | * | 4/1995 |
| JP | 11-302261 A | | 11/1999 |

* cited by examiner

*Primary Examiner*—Deepak Rao
(74) *Attorney, Agent, or Firm*—Birch, Stewart, Kolasch & Birch, LLP

(57) ABSTRACT

The present invention relates to a 6-(1-fluoroethyl)-5-iodo-4-aminopyrimidine compound represented by the following formula (1):

(1)

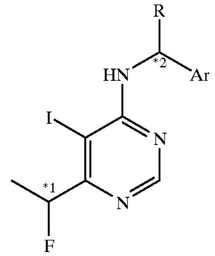

wherein Ar represents a phenyl group, a naphthyl group, a thienyl group, an indanyl group or a 1,4-benzodioxan-6-yl group, which is unsubstituted or substituted by 1 to 3 substituents selected from the group consisting of a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms and a phenoxy group; R represents a hydrogen atom or an alkyl group having 1 to 4 carbon atoms; *1 represents an asymmetric carbon atom; *2 represents an asymmetric carbon atom when R represents an alkyl group having 1 to 4 carbon atoms, a process for preparing the same, and agricultural and horticultural chemicals for controlling noxious organisms.

7 Claims, No Drawings

6-(1-FLUOROETHYL)-5-IODO-4-AMINOPYRIMIDINE COMPOUNDS PROCESS FOR PREPARATION OF THE SAME AND PEST CONTROLLERS FOR AGRICULTURAL AND HORTICULTURAL USE

This application is the national phase under 35 U.S. §371 of PCT International Application No. PCT/JP02/00064 which has an International filing date of Jan. 10, 2002, which designates the United States of America.

TECHNICAL FIELD

The present invention relates to a novel 6-(1fluoroethyl)-5-iodo-4-aminopyrimidine compound useful as agricultural and horticultural chemicals for controlling noxious organisms.

BACKGROUND ART

The 6-(1-fluoroethyl)-5-iodo-4-aminopyrimidine compound of the present invention is a novel compound and it has not been known that it has agricultural and horticultural effects of controlling noxious organisms.

An object of the present invention is to provide a novel 6-(1-fluoroethyl)-5-iodo-4-aminopyrimidine compound, a process for preparing the same and agricultural and horticultural chemicals for controlling noxious organisms containing the same as an effective ingredient.

DISCLOSURE OF THE INVENTION

The present inventors have studied to solve the above-mentioned problems, and as a result, they have found that novel 6-(1-fluoroethyl)-5-iodo-4-aminopyrimidine compounds have remarkable insecticidal, acaricidal, nematocidal and fungicidal effects for an agricultural and horticultural use, whereby they have accomplished the present invention.

That is, the present invention is as shown below.

The first invention relates to a 6-(1-fluoroethyl)-5iodo-4-aminopyrimidine compound represented by the following formula (1):

(1)

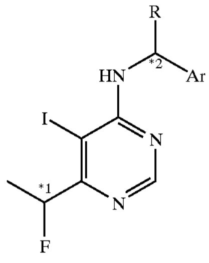

wherein Ar represents a phenyl group, a naphthyl group, a thienyl group, an indanyl group or a 1,4benzodioxan-6-yl group, which is unsubstituted or substituted by 1 to 3 substituents selected from the group consisting of a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms and a phenoxy group; R represents a hydrogen atom or an alkyl group having 1 to 4 carbon atoms; *1 represents an asymmetric carbon atom; *2 represents an asymmetric carbon atom when R represents an alkyl group having 1 to 4 carbon atoms.

The second invention relates to a process for preparing the 6-(1-fluoroethyl)-5-iodo-4-aminopyrimidine compound represented by the above-mentioned formula (1), which comprises reacting 4-chloro-6-(1-fluoroethyl)-5-iodopyrimidine represented by the following formula (2):

(2)

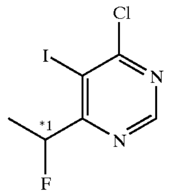

wherein *1 has the same meaning as defined above, with an amine represented by the following formula (3):

(3)

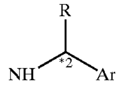

wherein Ar, R and *2 have the same meanings as defined above.

The third invention relates to an agricultural and horticultural chemicals for controlling noxious organisms containing the 6-(1-fluoroethyl)-5-iodo-4-aminopyrimidine compound represented by the above-mentioned formula (1) as an effective ingredient.

BEST MODE FOR CARRYING OUT THE INVENTION

In the following, the present invention will be explained in detail.

The respective substituents shown in the above-mentioned respective compounds are as mentioned below.

Ar is a phenyl group, a naphthyl group, a thienyl group, an indanyl group or a 1,4-benzodioxan-6-yl group, which is unsubstituted or substituted by 1 to 3 substituents selected from the group consisting of a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms and a phenoxy group.

R is a hydrogen atom or an alkyl group having 1 to 4 carbon atoms.

*1 is an asymmetric carbon atom.

*2 is an asymmetric carbon atom when R is an alkyl group having 1 to 4 carbon atoms.

As the halogen atom which is a substituent for Ar, there may be mentioned, for example, a chlorine atom, an iodine atom, a bromine atom, a fluorine atom, etc., and preferably a chlorine atom and a fluorine atom.

As the alkyl group having 1 to 4 carbon atoms which is a substituent for Ar, there may be mentioned, for example, a straight or branched alkyl group, and preferably a methyl group, an ethyl group, an isopropyl group and a t-butyl group.

As the haloalkyl group having 1 to 4 carbon atoms which is a substituent for Ar, there may be mentioned, for example, a difluoromethyl group, a trifluoromethyl group, 2,2,2-trifluoroethyl group, a 2-fluoroethyl group, etc., preferably a trifluoromethyl group.

As the alkoxy group having 1 to 4 carbon atoms which is a substituent for Ar, there may be mentioned, for example, a straight or branched alkoxy group, preferably a methoxy group and an ethoxy group.

As the haloalkoxy group having 1 to 4 carbon atoms which is a substituent for Ar, there may be mentioned, for example, a difluoromethoxy group, a trifluoromethoxy group, 2,2,2-trifluoroethoxy group, a 2-trifluoroethoxy group, etc., and preferably a difluoromethoxy group and a trifluoromethoxy group.

As the phenoxy group which is a substituent for Ar, there may be mentioned, for example, a phenoxy group which may be substituted by the above-mentioned halogen atom, the alkyl group having 1 to 4 carbon atoms, the haloalkyl group having 1 to 4 carbon atoms, the alkoxy group having 1 to 4 carbon atoms or a haloalkoxy group having 1 to 4 carbon atoms, preferably an unsubstituted phenoxy group.

A number of these substituents is preferably 1 to 3.

As the alkyl group having 1 to 4 carbon atoms of R, there may be mentioned, for example, a straight or branched alkyl group, and preferably a methyl group, an ethyl group, an i-propyl group, a n-butyl group and an i-butyl group.

The compound (1) of the present invention has an amino group so that an acid addition salt derived therefrom is also included in the present invention.

As an acid which forms an acid addition salt, there may be mentioned, for example, an inorganic acid such as hydrochloric acid, hydrobromic acid, nitric acid, sulfuric acid, phosphoric acid, etc.; a carboxylic acid such as formic acid, oxalic acid, fumaric acid, adipic acid, stearic acid, oleic acid, aconitic acid, etc.; a sulfonic acid such as methanesulfonic acid, benzenesulfonic acid, p-toluenesulfonic acid, etc.; saccharine, etc.

Also, the compound (1) of the present invention contains an asymmetric carbon atom represented by *1 and *2 so that the respective optical isomers, racemic isomers, diastereomers or a mixture thereof derived therefrom are each included in the present invention.

Among the compounds (1) of the present invention, particularly preferred compounds may include the following.

(1) A compound in which R is a hydrogen atom, and Ar is a phenyl group substituted by an alkoxy group having 1 to 4 carbon atoms. For example, there may be mentioned Compounds 5, 6, etc. shown in Table 1 mentioned below.

(2) A compound in which R is a hydrogen atom, and Ar is a phenyl group substituted by an alkyl group having 1 to 4 carbon atoms. For example, there may be mentioned Compounds 1, 2, 11, etc. shown in Table 1 mentioned below.

(3) A compound in which R is a hydrogen atom, and Ar is a phenyl group substituted by a phenoxy group. For example, there may be mentioned Compound 12, etc. shown in Table 1 mentioned below.

(4) A compound in which R is an alkyl group having 1 to 4 carbon atoms, and Ar is an unsubstituted phenyl group. For example, there may be mentioned Compounds 13 to 18, etc. shown in Table 1 mentioned below.

(5) A compound in which R is an alkyl group having 1 to 4 carbon atoms, and Ar is a phenyl group substituted by a haloalkoxy group having 1 to 4 carbon atoms and a halogen atom. For example, there may be mentioned Compound 22, etc. shown in Table 1 mentioned below.

(6) A compound in which R is an alkyl group having 1 to 4 carbon atoms, and Ar is a phenyl group substituted by a haloalkoxy group having 1 to 4 carbon atoms. For example, there may be mentioned Compounds 20, 21, 23, etc. shown in Table 1 mentioned below.

(7) A compound in which R is an alkyl group having 1 to 4 carbon atoms, and Ar is a phenyl group substituted by a halogen atom. For example, there may be mentioned Compounds 24, 25, etc. shown in Table 1 mentioned below.

(8) A compound in which R is an alkyl group having 1 to 4 carbon atoms, and Ar is a phenyl group substituted by an alkyl group having 1 to 4 carbon atoms. For example, there may be mentioned Compounds 27, 28, etc. shown in Table 1 mentioned below.

(9) A compound in which R is an alkyl group having 1 to 4 carbon atoms, and Ar is an unsubstituted indanyl group. For example, there may be mentioned Compounds 36, 37, etc. shown in Table 1 mentioned below.

(10) A compound in which R is an alkyl group having 1 to 4 carbon atoms, and Ar is an unsubstituted 1,4-benzodioxan-6yl group. For example, there may be mentioned Compound 39, etc. shown in Table 1 mentioned below.

(11) A compound in which R is a hydrogen atom, and Ar is a phenyl group substituted by a halogen atom. For example, there may be mentioned Compounds 3, 7, 8, etc. shown in Table 1 mentioned below.

(12) A compound in which R is a hydrogen atom, and Ar is a phenyl group substituted by a haloalkyl group having 1 to 4 carbon atoms. For example, there may be mentioned Compound 4, etc. shown in Table 1 mentioned below.

(13) A compound in which R is an alkyl group having 1 to 4 carbon atoms, and Ar is an unsubstituted naphthyl group. For example, there may be mentioned Compound 29, etc. shown in Table 1 mentioned below.

(14) A compound in which R is an alkyl group having 1 to 4 carbon atoms, and Ar is an unsubstituted thienyl group. For example, there may be mentioned Compound 33, etc. shown in Table 1 mentioned below.

A synthetic method of the above-mentioned compound (1) according to the present invention is described in detail.

Synthetic Method

Compound (1) is synthesized by reacting Compound (2) with Compound (3) in a solvent, in the presence of a base.

As a kind of the solvent, it is not particularly limited so long as it does not directly participate in the present reaction, and there may be mentioned, for example, a chlorinated or not chlorinated aromatic, aliphatic or alicyclic hydrocarbon such as benzene, toluene, xylene, methylnaphthalene, petroleum ether, ligroin, hexane, chlorobenzene, dichlorobenzene, chloroform, dichloroethane, trichloroethylene, etc.; an ether such as tetrahydrofuran, dioxane, diethyl ether, etc.; a nitrile such as aceto-nitrile, propionitrile, etc.; a ketone such as acetone, methyl ethyl ketone, etc.; an aprotic polar solvent such as N,N-dimethylformamide, dimethylsulfoxide, sulforane, N,N-dimethylimidazolidinone, N-methylpyrrolidone, etc.; and a mixture of the above-mentioned solvents.

An amount of the solvent to be used is preferably such that the content of Compound (2) becomes 5 to 80% by weight; and more preferably 10 to 70% by weight.

A kind of the base is not specifically limited, and an organic base and an inorganic base are mentioned. There may be mentioned, for example, a tertiary amine such as triethylamine, an organic base such as DBU, an inorganic base such as a hydride, hydroxide, carbonate, hydrogen carbonate of an alkali metal or an alkaline earth metal; and preferably an organic base such as triethylamine.

An amount of the base to be used is preferably 1 to 5-fold mol, more preferably 1.2 to 2.0-fold mol based on the amount of Compound (2).

A reaction temperature is not specifically limited, and it is preferably within the temperature range from a room temperature to a boiling point or less of the solvent to be used, particularly preferably 60 to 110° C.

A reaction time may vary depending on the above-mentioned concentration and temperature, and generally 0.5 to 8 hours.

An amount of the starting compound to be used is preferably 1.0 to 5-fold mol of Compound (3) based on the amount of Compound (2), and more preferably 1 to 1.1-fold mol.

Compound (2) to be used in the present invention can be prepared by the method shown in the following scheme according to the description of Japanese Patent Application No. 2000-384776.

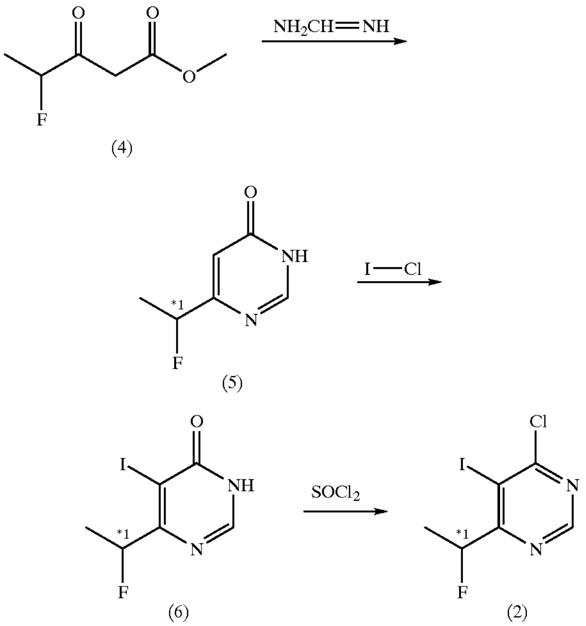

(4) (5) (6) (2)

wherein *1 has the same meaning as defined above.

Compound (4) can be prepared, for example, by the method according to Japanese Provisional Patent Application No. 171834/1999.

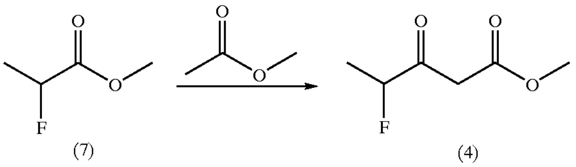

(7) (4)

Compound (3) may be a commercially available product or may be prepared by the method shown in the following scheme.

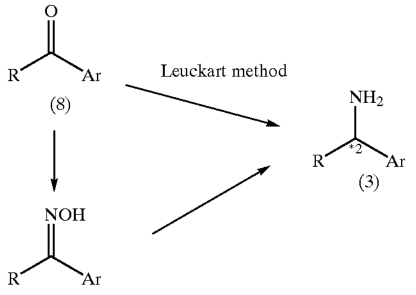

(8) (9) (3)

wherein Ar, R and *2 have the same meanings as defined above.

The desired Compound (1) prepared as mentioned above may be subjected to usual post-treatment such as extraction, concentration, filtration, etc. after completion of the reaction, and, if necessary, may be subjected to purification by the known methods such as recrystallization, various kinds of chromatographies, etc.

Controlling Effects

As the agricultural and horticultural noxious organisms on which a controlling effect by the compound (1) of the present invention can be observed, there may be mentioned agricultural and horticultural noxious insects [e.g. *Hemiptera* (planthoppers, leafhoppers, aphides, whiteflies, etc.), *Lepidoptera* (cabbage armyworms, diamond-back moth, leaf roller moths, pyralid moths, codling moths, cabbage butterfly, etc.), Coleoptera Tenebrionid beetles, leafbeetles, weevils, scarabs, etc.), *Acarina* (citrus red mite, two-spotted spider mite, etc. of *Tetranychidae* family, pink citrus rust mite of Eriophyidae family, etc.)], nematodes (e.g. root knot nematodes, cystcid nematodes, root lesion nematode , white-tip nematodes, pine wood nematodes), bulb mite in soil, hygienically noxious insects (e.g. flies, mosquitoes, cockroaches, etc.), noxious insects of stored grains (e.g. rust-red flour beetles, bean weevils, etc.), wood insects (e.g. termite such as Formosan subterranean termite, *Reticulitermes separatus* and *Cryptotermes domesticus*; powderpost beetles, drugstore beetles, carpenter moths, long-horned beetle, bark beetles, etc.) and also agricultural and horticultural diseases (e.g. *monilia furcticola*, wheat brown rust, barley powdery mildew, cucumber downy mildew, rice blast (*pyricularia ozyzea*), tomato late blight, etc.).

Chemical for Controlling Noxious Organisms

The agricultural and horticultural chemical for controlling noxious organisms of the present invention has particularly remarkable in insecticidal, acaricidal and nematocidal effects, and contains one or more kinds of Compound (1) as an effective ingredient.

Compound (1) may be used singly, however, it is generally preferred to use the same by formulating a carrier, surfactant, dispersant, auxiliary, etc. (for example, it is prepared as a composition such as dust powder, an emulsifiable concentrate, a fine granule, a granule, a wettable powder, an oily suspension, an aerosol, etc.) according to the conventionally known method.

As the carrier, there may be mentioned, for example, a solid carrier such as talc, bentonite, clay, kaolin, diatomaceous earth, white carbon, vermiculite, calcium hydroxide, siliceous sand, ammonium sulfate, urea, etc., a liquid carrier such as hydrocarbon (kerosine, mineral oil, etc.), aromatic hydrocarbon, (benzene, toluene, xylene, etc.), chlorinated hydrocarbon (chloroform, carbon tetrachloride, etc.), ethers (dioxane, tetrahydrofuran, etc.), ketones (acetone, cyclohexanone, isophorone, etc.), esters (ethyl acetate, ethyleneglycol acetate, dibutyl maleate, etc.), alcohols (methanol, n-hexanol, ethylene glycol, etc.), aprotic polar solvent (dimethylformamide, dimethylsulfoxide, etc.), water, etc.; a gas carrier such as air, nitrogen, a carbon dioxide gas, fleone, etc. (in this case, mixture spreading can be carried out), and the like.

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. As a surfactant, there may be used commercially available products, for example, Neopelex powder (trade name, produced by Kao K. K.), Demol (trade name, produced by Kao K. K.), Toxanone (trade name, produced by Sanyo Chemical Industries, Ltd.) and the like. Further, for improving properties of its formulation, for example, carboxymethyl cellulose, polyethylene glycol and gum arabic can be used as an auxiliary.

In preparation of the present chemical, the above-mentioned carrier, surfactant, dispersant and auxiliary can be used singly or in a suitable combination, respectively, depending on the respective purposes.

When the compound (1) of the present invention is made into formulations, the concentration of the active ingredient is generally 1 to 50% by weight in an emulsifyable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to a suitable concentration and spraying them to stems and leaves of plants, soil and paddy field surface, or by applying them directly thereto, depending on the purposes.

EXAMPLE

In the following, the present invention will be explained specifically by referring to Reference examples and Examples. Incidentally, these will not limit the scope of the present invention.

Reference Example 1 (Synthetic Method of Compound (5))

Synthesis of 6-(1-fluoroethyl)-4-pyrimidone

In methanol (1000 ml) was dissolved methyl 4-fluoro3-oxopentanoate (93.3 g), and a 28% sodium methylate/methanol solution (365 g) and formamidine acetate (98.4 g) were successively added to the solution, and the resulting mixture was refluxed at 40° C. for 12 hours.

After completion of the reaction, the mixture was cooled to 10° C. or lower, and a mixture of conc. sulfuric acid (95.1 g) and water (85 g) was added to the above mixture. Then, the mixture was stirred at 50° C. for 30 minutes, insoluble materials were removed by filtration, and the filtrate was concentrated under reduced pressure. The resulting residue was recrystallized from isopropanol to obtain 58 g of the desired compound as colorless crystal.

m.p. 170.0 to 171.5° C.

Reference Example 2 (Synthetic Method of Compound (6))

Synthesis of 6-(1-fluoroethyl)-5-iodo-4-pyrimidone

To an acetic acid (150 ml) solution of 6-(1fluoroethyl)-4-pyrimidone (56.8 g) was added dropwise under room temperature and stirring an acetic acid solution of iodine monochloride prepared by adding iodine (50.8 g) to acetic acid (500 ml) and blowing chlorine (15 g) thereinto under room temperature and stirring, and the resulting mixture was stirred for 6 hours.

After completion of the reaction, the acetic acid was removed under reduced pressure, water (300 ml) was added to the residue to dissolve the material, and pH of the mixture was adjusted to 5 with 2N sodium hydroxide and an aqueous saturated sodium hydrogen carbonate solution. The precipitated crystals were collected by filtration, washed with water and dried to obtain 85 g of the desired product as pale ocherous crystal.

Moreover, the crystal was purified by recrystallization from ethyl acetate-hexane to obtain 76.0 g of the desired product as colorless needle-like crystal.

m.p. 195 to 196° C.

Reference Example 3 (Synthetic Method of Compound (2))

Synthesis of 4-chloro-6-(1-fluoroethyl)-5-iodopyrimidine

To ethyl acetate (180 ml) was added 6-(1-fluoroethyl)-5-iodo-4-pyrimidone (53.6 g), N,N-dimethylformamide (1.5 g) was added to the mixture and the resulting mixture was stirred at 70° C. while heating. Subsequently, thionyl chloride (28.6 g) was added dropwise to the mixture and stirred for 3 hours to complete the reaction.

After cooling the reaction mixture, the mixture was poured into ice-cold water, and pH of the mixture was adjusted to 4 with 2N sodium hydroxide. The ethyl acetate layer was collected by separation, washed with water, and then, dried over anhydrous sodium sulfate. Subsequently, under reduced pressure, the solvent was removed by distillation, and the obtained residue was purified by distillation under reduced pressure to obtain 54.6 g of the desired compound as a pale yellowish liquid.

b.p. 116 to 118° C./4 mmHg

Example 1 (Synthetic Method of Compound (1))

(1) Synthesis of 4-(4-t-butylbenzylamino)-6-(1-fluoroethyl)-5-iodopyrimidine (Compound 1)

In 20 ml of toluene were dissolved 4-t-butylbenzyl-amine (0.8 g) and triethylamine (0.6 g), and 4-chloro-6-(1-fluoroethyl)-5-iodopyrimidine (1.5 g) was added to the solution and the resulting mixture was stirred at about 80° C. for 3 hours.

After completion of the reaction, triethylamine hydrochloride was removed by filtration, the solvent was removed under reduced pressure, and the obtained residue was purified by silica gel column chromatography (Wako gel C-200, eluent; n-hexane/ethyl acetate=3/1) to obtain 1.5 g of the objective product as colorless small plate-shaped crystal.

m.p. 114 to 115° C.; $^1$H-NMR ($CDCl_3$, δ ppm); 1.32 (9H, s), 1.61 to 1.71 (3H, d-d), 4.68 to 4.70 (2H, d), 3.74 to 3.81 (2H, q), 5.70 to 5.92 (1H, d-q), 5.76 (1H, b), 7.26 to 7.41 (4H, m), 8.50 (1H, s).

(2) Synthesis of 6-(1-fluoroethyl)-5-iodo-4-(α-methylbenzylamino)pyrimidine (Compound 13)

In 40 ml of toluene were dissolved α-methylbenzyl-amine (1.2 g) and triethylamine (1.2 g), and 4-chloro-6-(1-fluoroethyl)-5-iodopyrimidine (2.9 g) was added to the solution and the resulting mixture was stirred at about 80° C. for 3 hours.

After completion of the reaction, triethylamine hydrochloride was removed by filtration, the solvent was removed under reduced pressure, and the obtained residue was purified by silica gel column chromatography (Wako gel C-200, eluent; n-hexane/ethyl acetate=3/1) to obtain 2.9 g of the desired product as a pale orange viscous liquid.

$^1$H-NMR ($CDCl_3$, δ ppm); 1.57 to 1.69 (6H, m), 4.68 to 4.70 (2H, d), 5.24 to 5.92 (1H, d-q), 5.83 (1H, b), 7.24 to 7.37 (5H, m), 8.43 (1H, s).

(3) Synthesis of other Compound (1) in Table 1

According to the methods described in the above-mentioned (1) and (2), other compounds (1) in Table 1 were synthesized.

The compounds (1) synthesized as mentioned above and their physical properties are shown in Table 1.

*1 is all racemic mixtures (R,S).

TABLE 1

(1)

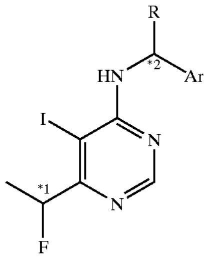

| Compound | Ar | R | *2 | Physical property |
|---|---|---|---|---|
| 1 | 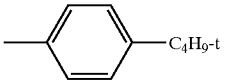 | H | R, S | m.p.114~ 115° C. |
| 2 | 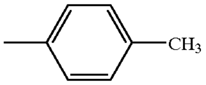 | H | R, S | m.p.80~ 81° C. |
| 3 | 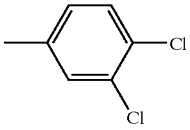 | H | R, S | m.p.105~ 106° C. |
| 4 | 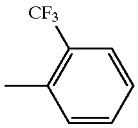 | H | R, S | m.p.112~ 113° C. |
| 5 | 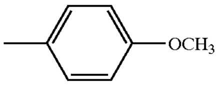 | H | R, S | $n_D^{21.9}$ 1.6089 |
| 6 | 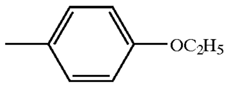 | H | R, S | m.p.82~ 63° C. |
| 7 | 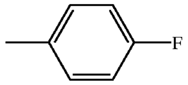 | H | R, S | m.p.72~ 73° C. |

TABLE 1-continued (1)

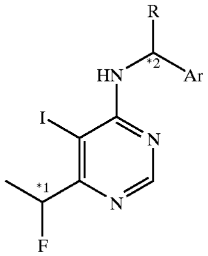

| Compound | Ar | R | *2 | Physical property |
|---|---|---|---|---|
| 8 | 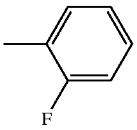 | H | R, S | m.p.69~ 71° C. |
| 9 | 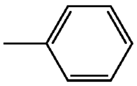 | H | R, S | |
| 10 | 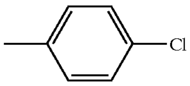 | H | R, S | |
| 11 | 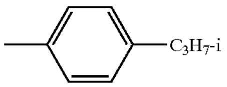 | H | R, S | m.p.62~ 63° C. |
| 12 | 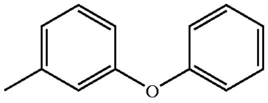 | H | R, S | $n_D^{18.8}$ 1.6145 |
| 13 | 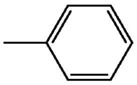 | $CH_3$ | R, S | $n_D^{22.9}$ 1.6053 |
| 14 | 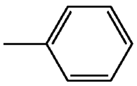 | $CH_3$ | S | $n_D^{22.3}$ 1.6061 |
| 15 | 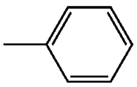 | $CH_3$ | R | $n_D^{23.2}$ 1.6065 |
| 16 | 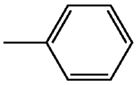 | $C_2H_5$ | R, S | $n_D^{23.1}$ 1.5993 |
| 17 | 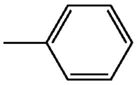 | $C_4H_9$-n | R, S | $n_D^{18.9}$ 1.5827 |
| 18 | 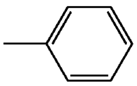 | $C_4H_9$-i | R, S | $n_D^{23.7}$ 1.5831 |

TABLE 1-continued
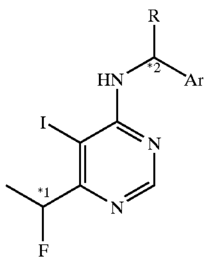
(1)
| Compound | Ar | R | *2 | Physical property |
|---|---|---|---|---|
| 19 | 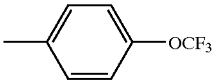 | $CH_3$ | R, S | |
| 20 | 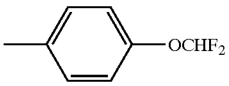 | $C_2H_5$ | R, S | $n_D^{22.5}$ 1.5645 |
| 21 | 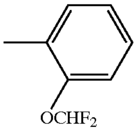 | $C_2H_5$ | R, S | unable to measure |
| 22 | 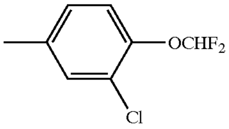 | $CH_3$ | R, S | $n_D^{23.4}$ 1.5755 |
| 23 | 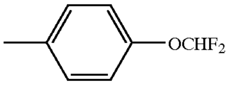 | $CH_3$ | R, S | $n_D^{22.5}$ 1.5675 |
| 24 | 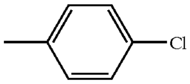 | $C_2H_5$ | R, S | $n_D^{23.1}$ 1.6002 |
| 25 | 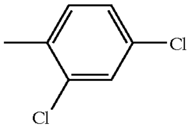 | $CH_3$ | R, S | $n_D^{23.7}$ 1.6006 |
| 26 | 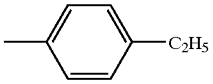 | $CH_3$ | R, S | $n_D^{23.6}$ 1.5936 |
| 27 | 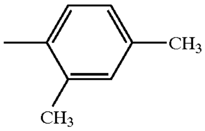 | $CH_3$ | R, S | $n_D^{23.7}$ 1.5842 |
TABLE 1-continued
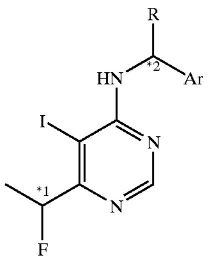
(1)
| Compound | Ar | R | *2 | Physical property |
|---|---|---|---|---|
| 28 | 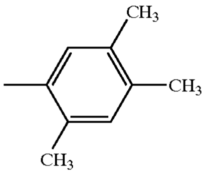 | $CH_3$ | R, S | $n_D^{23.5}$ 1.5837 |
| 29 | 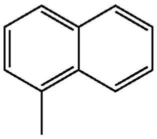 | $CH_3$ | R, S | m.p.110~112° C. |
| 30 | 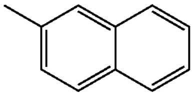 | $CH_3$ | R, S | |
| 31 | 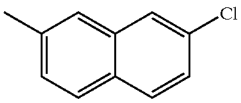 | $C_2H_5$ | R, S | |
| 32 | 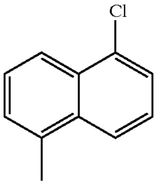 | $CH_3$ | R, S | |
| 33 | 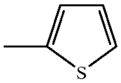 | $CH_3$ | R, S | $n_D^{23.3}$ 1.6105 |
| 34 | 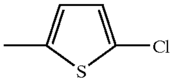 | $CH_3$ | R, S | |
| 35 | 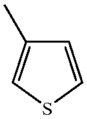 | $CH_3$ | R, S | |
| 36 | 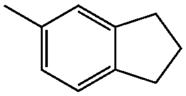 | $CH_3$ | R, S | $n_D^{19.5}$ 1.5923 |

TABLE 1-continued (1)

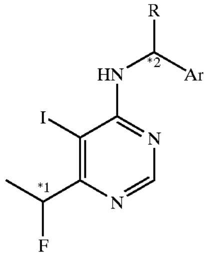

| Compound | Ar | R | *2 | Physical property |
|---|---|---|---|---|
| 37 | 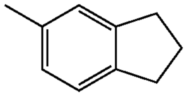 | $C_2H_5$ | R, S | $n_D^{19.3}$ 1.5856 |
| 38 | 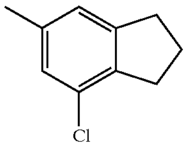 | $CH_3$ | R, S | |
| 39 | 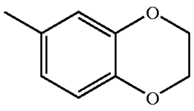 | $CH_3$ | R, S | $n_D^{19.1}$ 1.5835 |
| 40 | 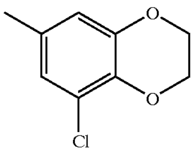 | $CH_3$ | R, S | |

Example 2 (Preparation of Formulations)

(1) Preparation of Granule

Five parts by weight of Compound (1) were uniformly mixed with 35 parts by weight of bentonite, 57 parts by weight of talc, 1 part by weight of Neopelex powder (trade name, produced by Kao K. K.) and 2 parts by weight of sodium lignosulfonate, then the mixture was kneaded with addition of a small amount of water, followed by granulation and drying, to obtain a granule.

(2) Preparation of Wettable Powder

Ten parts by weight of Compound (1) were uniformly mixed with 70 parts by weight of kaolin, 18 parts by weight of white carbon, 1.5 parts by weight of Neopelex powder (trade name, produced by Kao K. K.) and 0.5 part by weight of Demol (trade name, produced by Kao K. K.), then the mixture was pulverized to obtain a wettable powder.

(3) Preparation of Emulsifiable Concentrate

Twenty parts by weight of Compound (1) were uniformly mixed with 70 parts by weight of xylene by adding 10 parts by weight of Toxanone (trade name, produced by Sanyo Chemical Industries, Ltd.), and mixed therein uniformly to obtain an emulsifiable concentrate.

(4) Preparation of Dustable Powder

Five parts by weight of Compound (1) were uniformly mixed with 50 parts by weight of talc and 45 parts by weight of kaolin to obtain dustable powder.

Example 3 (Tests of Effects)

(1) Test of Effect on Green Caterpillar (Common Cabbage Worm)

The respective wettable powders of Compounds (1) shown in Table 1 prepared as in Example 2 were diluted to 1000 ppm with water containing a surfactant (0.01%), and in these respective chemical solutions, cabbage leaves (5×5 cm) were dipped for 30 seconds, and each leaf was put into the respective plastic cups and air-dried.

Subsequently, 10 green caterpillars (3rd instar larvae) were placed in the respective cups, which were sealed by lids, and they were left to stand in a thermostat chamber at 25° C. After 2 days, insecticidal rate was determined by counting living and dead insects in the respective cups.

As a result, Compounds 1 to 8, 11 to 18, 20 to 29, 33, 36, 37, 39 showed the insecticidal effect of 80% or more.

(2) Test of Effect on Green Peach Aphid

The respective wettable powders of Compounds (1) shown in Table 1 prepared as in Example 2 were diluted to 100 ppm with water containing a surfactant (0.01%), and in these respective chemical solutions, cabbage leaves (5×5 cm) were dipped for 30 seconds, and each leaf was put into the respective plastic cups and air-dried.

Subsequently, 10 green peach aphids (apterous female adults) were placed in the respective cups, which were sealed by lids, and they were left to stand in a thermostat chamber at 25° C. After 3 days, insecticidal rate was determined by counting living and dead apterous female adults and larvaes in the respective cups.

As a result, Compounds 6, 11 to 14, 16, 22 to 25, 27, 28, 37 and 39 showed the insecticidal effect of 80% or more.

(3) Antibacterial Test

Acetone solutions of Compounds (1) shown in Table 1 were migrated into a PDA (potato dextrose agar) medium with a final concentration of 40 ppm to prepare plate culture media.

Respective colonies of *monilia furcticola* and *pyricularia oryzea* each previously grown in PDA plate culture media were cut with 1 mm square by a scalpel and inoculated to plate culture media containing chemicals.

They were cultured at 25° C. under dark place for 3 days, and the diameter of the colony was compared to those grown in the area to which no chemical was added, and a colony growth-inhibiting ratio (%) was calculated by the following equation.

$$\text{Colony growth inhibiting ratio (\%)} = \left(1 - \frac{\text{Diameter (mm) of colony grown in chemical treated area}}{\text{Diameter (mm) of colony grown in chemical non-treated area}}\right) \times 100$$

Judgment of the effects was carried out with 6 ranks from 5 to 0 in which a colony growth-inhibiting ratio of 95 to 100% was rated 5, 85 to 95% was 4, 85 to 70% was 3, 45 to 70% was 2, 10 to 45% was 1, and 10 to 0% was 0.

As a result, Compounds 2 to 8, 11 to 18, 20 to 29, 33, 36, 37 and 39 showed effects of 4 or more against *monilia furcticola*, and Compounds 1 to 8, 11 to 18, 20 to 29, 33, 37 and 39 showed effects of 4 or more against *pyricularia oryzea*.

Industrial Applicability

The novel 6-(1-fluoroethyl)-5-iodo-4-aminopyrimidine compound of the present invention has excellent effects of controlling noxious organisms for an agricultural and horticultural use.

What is claimed is:

1. A 6-(1-fluoroethyl)-5 iodo-4-aminopyrimidine compound represented by the following formula (1):

(1)

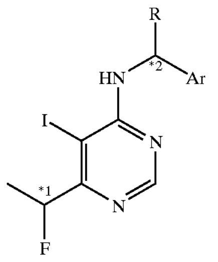

wherein Ar represents a phenyl group, a naphthyl group, a thienyl group, an indanyl group or a 1,4-benzodioxan-6-yl group, which is unsubstituted or substituted by 1 to 3 substituents selected from the group consisting of a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms and a phenoxy group; R represents a hydrogen atom or an alkyl group having 1 to 4 carbon atoms; *1 represents an asymmetric carbon atom *2 represents an asymmetric carbon atom when R represents an alkyl group having 1 to 4 carbon atoms.

2. The 6-(1-fluoroethyl)-5-iodo-4-aminopyrimidine compound according to claim 1, wherein Ar in the above mentioned formula (1) is a phenyl group substituted by 1 to 3 substituents selected from the group consisting of a halogen atom, an alkyl group having 1 to 4 carbon atoms, a halo-alkyl group having 1 to 4 carbon atoms, an alkoxy group having 1 to 4 carbon atoms, a haloalkoxy group having 1 to 4 carbon atoms and a phenoxy group, or an unsubstituted phenyl group.

3. The 6-(1-fluoroethyl)-5-iodo-4-aminopyrimidine compound according to claim 1, wherein the substituent for Ar is selected from the group consisting of a chlorine atom, a fluorine atom, a methyl group, an ethyl group, an isopropyl group, a t-butyl group, a trifluoromethyl group, a methoxy group, an ethoxy group, a difluoromethoxy group, a trifluoromethoxy group and an unsubstituted phenoxy group.

4. The 6-(1-fluoroethyl)-1)-5-iodo-4-aminopyrimidine compound according to claim 1, wherein R is a hydrogen atom, a methyl group, an ethyl group, an I-propyl group, a n-butyl group or an I-butyl group.

5. The 6-(1-fluoroethyl)-5-iodo-4-aminopyrimidine compound according to claim 1, wherein Ar represents an phenyl group substituted with an alkyl group having 1 to 4 carbon atoms and R is a hydrogen atom or an alkyl group having 1 to 4 carbon atoms.

6. A process for preparing the 6-(1-fluoroethyl)-5-iodo-4-aminopyrimidine compound represented by the formula (1) according to claim 1, which comprises reacting 4-chloro-6-(1- fluoroethyl)-5-iodopyrimidine represented by the following formula (2):

(2)

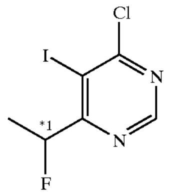

wherein *1 has the same meaning as defined in claim 1, with an amine represented by the following formula (3):

(3)

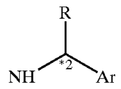

wherein Ar, R and *2 have the same meanings as define in claim 1.

7. An agricultural or horticultural composition for controlling noxious organisms comprising the 6-(1-fluoroethyl)-5 -iodo-4 -aminopyrimidine compound represented by the formula (1) according to claim 1 as an effective ingredient, and a carrier.

* * * * *